United States Patent
Potts et al.

(10) Patent No.: US 6,812,169 B2
(45) Date of Patent: *Nov. 2, 2004

(54) ABSORBENT ARTICLE WITH FLUID TREATMENT AGENT

(75) Inventors: David Charles Potts, Dunwoody, GA (US); Jack Nelson Lindon, Alpharetta, GA (US); Emmanuelle Cecile Damay, Roswell, GA (US); Dmitry Yavich, Neenah, WI (US); Matthew David Young, Kennesaw, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 249 days.

This patent is subject to a terminal disclaimer.

(21) Appl. No.: 10/035,701

(22) Filed: Nov. 9, 2001

(65) Prior Publication Data

US 2002/0065495 A1 May 30, 2002

Related U.S. Application Data

(63) Continuation of application No. 09/183,170, filed on Oct. 30, 1998, now Pat. No. 6,350,711.

(51) Int. Cl.$^7$ ......................... B32B 27/04; B32B 27/12; B32B 5/02; D04H 1/00
(52) U.S. Cl. ..................... 442/118; 442/121; 442/123; 442/286; 442/327; 442/394; 442/417
(58) Field of Search ................................ 442/118, 121, 442/123, 286, 327, 394, 417

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,167,464 A | 9/1979 | George | |
| 4,190,563 A | 2/1980 | Bosley et al. | |
| 4,340,563 A | 7/1982 | Appel et al. | |
| 4,358,394 A | 11/1982 | Crews et al. | |
| 4,462,989 A | 7/1984 | Cerami | |
| 4,488,928 A | 12/1984 | Ali Khan et al. | |
| 4,565,663 A | 1/1986 | Errede et al. | |
| 4,614,787 A | 9/1986 | Szycher et al. | |
| 4,616,644 A | * 10/1986 | Saferstein et al. | ............ 602/48 |
| 5,108,827 A | 4/1992 | Gessner | |
| 5,190,657 A | 3/1993 | Heagle et al. | |
| 5,281,208 A | 1/1994 | Thompson et al. | |
| 5,336,552 A | 8/1994 | Strack et al. | |
| 5,382,400 A | 1/1995 | Pike et al. | |
| 5,460,622 A | 10/1995 | Dragoo et al. | |
| 5,486,167 A | 1/1996 | Dragoo et al. | |
| 5,529,933 A | 6/1996 | Young et al. | |
| 5,558,834 A | 9/1996 | Chu et al. | |
| 5,700,254 A | 12/1997 | McDowall et al. | |
| 5,759,844 A | 6/1998 | Hiraki et al. | |
| 5,762,871 A | 6/1998 | Neyer | |
| 5,797,891 A | 8/1998 | Wiersma | |
| 5,853,628 A | * 12/1998 | Varona | ......................... 264/6 |
| 6,017,832 A | 1/2000 | Yahiaoui et al. | |
| 6,060,636 A | 5/2000 | Yahiaoui et al. | |
| 6,177,367 B1 | 1/2001 | Mathis | |
| 6,221,460 B1 | * 4/2001 | Weber et al. | ............... 428/131 |
| 6,231,557 B1 | 5/2001 | Krautkramer et al. | |
| 2001/0018068 A1 | 8/2001 | Lorenzi et al. | |
| 2002/0040210 A1 | 4/2002 | Luccio et al. | |

FOREIGN PATENT DOCUMENTS

| | | |
|---|---|---|
| EP | 019 371 | 11/1980 |
| EP | 793 971 | 9/1997 |
| WO | WO 93/21879 | 11/1993 |
| WO | 96/40300 | 12/1996 |
| WO | WO 97/24378 | 7/1997 |
| WO | WO 98/09662 | 3/1998 |
| WO | WO 98/10134 | 3/1998 |
| WO | WO 99/12505 | 3/1999 |
| WO | 99/32706 | 7/1999 |
| WO | WO 99/61079 | 12/1999 |
| WO | WO 00/25835 | 5/2000 |
| WO | WO 01/00156 | 1/2001 |
| WO | WO 01/45615 A1 | 6/2001 |
| WO | WO 02/45762 | 6/2002 |

* cited by examiner

Primary Examiner—Arti R. Singh
Assistant Examiner—Christopher Pratt
(74) Attorney, Agent, or Firm—Pauley Petersen & Erickson

(57) ABSTRACT

A personal care absorbent article, such as a sanitary pad or napkin, wound dressing, and the like having an absorbent material treated with a fluid treatment agent, which fluid treatment agent causes red blood cells in a blood-containing fluid to agglomerate or lyse as the fluid passes into and/or through the absorbent article. In accordance with one preferred embodiment, the absorbent material is a porous nonwoven web material.

46 Claims, No Drawings

ABSORBENT ARTICLE WITH FLUID TREATMENT AGENT

This is a continuation of U.S. patent application Ser. No. 09/183,170, filed 30 Oct. 1998 now U.S. Pat. No. 6,350,711.

BACKGROUND OF THE INVENTION

1. Field of the Invention

This invention relates to an absorbent material for absorbing blood-containing fluids. More particularly, this invention relates to an absorbent material for use in personal care absorbent articles, which are particularly adapted for absorbing various blood-containing bodily fluids while providing comfort and fit to the wearer, such as catamenial articles such as sanitary napkins and pads, wound dressings, and the like. The absorbent material may be a woven material, nonwoven material or a combination of both woven and nonwoven materials.

2. Description of Prior Art

A wide variety of disposable absorbent articles for collecting bodily fluids are known in the art. Commercial absorbent articles include diapers, sanitary napkins, training pants, and incontinent care pads, wound dressings, and the like. Disposable products of this type include some functional elements for receiving, absorbing, and retaining fluids. Typically, such absorbent articles have an absorbent core containing cellulosic fibers, for example, wood pulp fluff, particles of highly absorbent materials, for example, superabsorbents, and an admixture of cellulosic fibers and superabsorbents. Typically, such articles include a fluid-permeable cover sheet or topsheet which typically faces the body of the user, an absorbent core, and a fluid-impermeable backsheet.

Cover sheet materials are utilized for the transport of bodily fluids into the absorbent core of personal care absorbent articles and, thus, materials used for cover sheet applications must manage distinctly different body excretions, depending upon the application and the product type. Some products must manage fluids, such as urine, while others must manage proteinaceous and viscoelastic fluids, such as menstrual discharge and fecal matter. The management of viscoelastic menstrual discharge by feminine care products such as sanitary pads and napkins is exacerbated due to the variations in composition and rheology over a broad range of elasticity. Fluid management in feminine care applications requires control of absorption of bodily fluids, control of fluid retention in the cover, control of stain size and intensity, control of rewet of fluid back to the surface, and control of the release of fluid to the absorbent core.

There are several factors which influence the flow of liquids in fibrous structures including the geometry of the pore structure in the fabrics, the nature of the solid surface (surface energy, surface charge, etc.), the geometry of the solid surface (surface roughness, grooves, etc.), the chemical/physical treatment of the solid surface, and the chemical nature of the fluid. One problem associated with absorbent articles intended for use in handling fluids comprising blood components such as feminine care products and wound dressings is the tendency of red blood cells to block the pores of the materials used for absorption of fluids in such products. Typical of such porous materials are nonwoven or fibrous web materials. The blockage of the pores of the nonwoven or fibrous web materials by the red blood cells results in a reduction in the fluid intake and the wicking capabilities of such products. In addition, in the case of feminine care products such as sanitary pads and napkins, the blockage of pores of nonwoven materials used therein by red blood cells results in increased staining. In the case of feminine care products comprising superabsorbents, the red blood cells attach themselves to the superabsorbents, resulting in blockage of the superabsorbents and a significant reduction in fluid uptake.

In the case of feminine care products such as sanitary pads and napkins, women have come to expect a high level of performance in terms of comfort and fit, retention of fluid, and minimal staining. Of utmost importance, leakage of fluid from the pad onto undergarments is regarded as totally unacceptable.

Improving the performance of feminine care products continues to be a formidable undertaking, although numerous improvements have been made in both their materials and structures. However, solutions addressing the issues arising from the presence of red blood cells in blood or menses in feminine care products, as well as other absorbent materials for handling blood-containing fluids, have not been satisfactorily implemented. It is apparent that a system which effectively handles red blood cells in a manner which addresses the issues set forth hereinabove will not only improve the distribution of incoming fluids by the absorbent material, but will also reduce the tendency toward premature failures of these absorbent articles.

Methods for separating or removing red blood cells from blood-containing fluids generally fall into two categories, agglutination (agglomeration) in which the red blood cells agglomerate, thereby enabling them to be more readily separated from the remaining fluid component, for example, by filtration, and lysing in which the membranes of the red blood cells are disrupted, resulting in a breaking down or breaking apart of the red blood cells. Agglomeration is known to occur, for example, in the presence of certain antibodies. However, we are unaware of any personal care absorbent articles employing these red blood cell management techniques.

SUMMARY OF THE INVENTION

Accordingly, it is one object of this invention to provide a blood-containing fluid absorbent material having the capability of reducing the level of red blood cells in the fluid.

It is one object of this invention to provide a feminine care absorbent product having improved fluid handling, including improved fluid intake and wicking, and reduced staining characteristics.

It is another object of this invention to provide a feminine care absorbent product having means for partitioning components of menses, thereby enabling improved fluid handling and reduced staining.

It is another object of this invention to provide a method and system which improves the intake of fluid by superabsorbents which may be present in feminine care absorbent products.

These and other objects of this invention are achieved by a material for absorbing a blood-containing fluid comprising an absorbent material treated with a fluid treatment agent whereby red blood cells within a blood-containing fluid absorbed by the absorbent material are agglomerated or lysed. In accordance with a particularly preferred embodiment, the absorbent material comprises a porous nonwoven web material treated with said fluid treatment agent. In accordance with one embodiment of this invention, the fluid treatment agent is an agglomerating agent which causes the red blood cells in the blood-containing fluid to agglomerate, thereby enabling them to be physically separated from the blood-containing fluid, leaving a fluid that is easier to absorb and less strongly colored. In accordance with another embodiment of this invention, the fluid treatment agent is a cell lysing agent.

The porous nonwoven web material may be produced by any number of means known to those skilled in the art. In accordance with one embodiment of this invention, the nonwoven web material comprises a gradient of pore sizes produced by layering of nonwoven web layers, each layer of which has an average pore size different from the average pore sizes of other nonwoven web layers, forming a porosity gradient nonwoven web material. When disposed between the cover sheet and the liquid impervious backing material of a personal care absorbent article, the porosity gradient nonwoven web material is disposed such that larger average pore sizes are oriented toward the cover sheet and the average pore size of the nonwoven web material decreases in the direction of the liquid impervious backing material. As a result, the porosity gradient nonwoven web material acts as a "depth filter" wherein the agglomerated red blood cells become trapped within the larger size pores of the porosity gradient nonwoven web material. However, care must be taken in selecting the pore size gradient to insure that the fluid separated from the agglomerated red blood cells is still able to pass by trapped particles or clumps of red blood cells, thereby enabling further distribution of the fluid within the personal care absorbent article as desired, for example, to a superabsorbent.

One of the benefits of this invention derives from the fact that the red blood cells of a blood-containing fluid, having come into contact with the fluid treatment agent, are no longer able to block the flow of fluids into the superabsorbents that may be present. This is particularly surprising in the case where the red blood cells are lysed because, unlike agglomerated cells which may become trapped within the pores of the nonwoven material, resulting in their separation from the remaining fluid components, i.e. plasma, the components of the lysed cells remain in the fluid but apparently are no longer able to attach themselves to the superabsorbents.

DESCRIPTION OF PREFERRED EMBODIMENTS

Definitions

As used herein, the term "nonwoven web" or "fibrous web" refers to any material comprising fibrous or fiber-like elements, usually in a random arrangement, joined by bonding points which stabilize the structure, providing at least some mechanical integrity, which form at least some small pores throughout the length and width thereof between adjacent fiber-like elements. The term also includes individual filaments and strands, yarns or tows as well as foams and films that have been fibrillated, apertured or otherwise treated to impart fabric-like properties. "Nonwoven webs" or "fibrous webs" are formed by many processes such as, for example, spunbonding, meltblowing, airlaid and bonded carded processes.

As used herein, the term "spunbonding" refers to a process in which small diameter fibers are formed by extruding molten thermoplastic materials as filaments from a plurality of fine, usually circular capillaries of a spinneret with the diameter of the extruded filaments then being rapidly reduced as, for example, described in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992, U.S. Pat. No. 3,341,394 to Kinney, U.S. Pat. No. 3,502,763 to Hartmann, U.S. Pat. No. 3,502,538 to Levy, and U.S. Pat. No. 3,542,615 to Dobo et al. Spunbond fibers are quenched and generally not tacky when they are deposited onto a collecting surface. Spunbond fibers are generally continuous and have average diameters frequently larger than 7 microns, more particularly, between about 10 and 20 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Such a process is disclosed, for example, by U.S. Pat. No. 3,849,241 to Butin. Meltblown fibers are microfibers which may be continuous or discontinuous and are generally smaller than 10 microns in average diameter.

As used herein, the term "bonded carded" or "bonded carded webs" refers to nonwoven webs formed by carding processes as are known to those skilled in the art and further described, for example, in U.S. Pat. No. 4,488,928 to Alikhan and Schmidt. Typically, carding processes involve starting with a blend of, for example, staple fibers with bonding fibers or other bonding components in a bulky batt that is combed or otherwise treated to provide a generally uniform basis weight. This web is heated or otherwise treated to activate the adhesive component, resulting in an integrated, usually lofty nonwoven material.

As used herein, the term "monocomponent" fiber refers to a fiber formed from one or more extruders using only one polymer. This is not meant to exclude fibers formed from one polymer to which small amounts of additives have been added for color, anti-static properties, lubrication, hydrophilicity, etc. These additives are generally present in an amount less than about 5 weight percent and more typically about 2 weight percent.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across a cross-section of the conjugate fibers and extend continuously along the length of the conjugate fibers. The configuration of such a conjugate fiber may be, for example, a sheath/core arrangement in which one polymer is surrounded by another, or may be a side-by-side arrangement, or an "islands-in-the-sea" arrangement. Conjugate fibers are taught, for example, by U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75, or any other desired ratios.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, syndiotactic, and random symmetries.

As used herein, the term "absorbent material" refers to any material having fluid absorption properties.

As used herein, the term "personal care absorbent articles" refers to diapers, training pants, absorbent underpants, adult incontinence products, sanitary wipes and feminine hygiene products such as sanitary napkins and pads.

As used herein, the term "intake" refers to the ability of an absorbent article to absorb fluid. Intake time is used to assess the quality of absorption with lower intake times denoting materials capable of rapid absorption and higher intake times denoting materials with poorer absorption.

As used herein, the term "stain" refers to fluid, wet or dry, which is present on the top surface, in, or on the bottom surface of a cover material or topsheet of a personal care absorbent article.

As used herein, the term "gradient porosity" refers to a porous system in which the average pore size in the system decreases (or increases) from one side of the system to the opposite side of the system. In the case of personal care absorbent articles employing porosity gradient nonwoven web materials in accordance with this invention, average pore sizes decrease from the side of the nonwoven web material disposed towards the topsheet or cover of the absorbent article in the direction of the liquid impervious backsheet.

This invention, in accordance with one embodiment, provides a nonwoven web material suitable for use in personal care absorbent articles such as sanitary pads, napkins and tampons, wound dressings and the like, the intended purpose of which is to absorb and store blood-containing fluids. The nonwoven web material of this invention reduces the impact of red blood cells on fluid intake, wicking capabilities, and staining. The nonwoven web material of this invention is a porous material which is treated with a fluid treatment agent whereby the red blood cells in a blood-containing fluid, such as menses, are either agglomerated or lysed.

In accordance with one preferred embodiment of this invention, the average pore size of the pores of the nonwoven web material is in the range of about 10 microns to about 200 microns, thereby ensuring that the individual red blood cells will be able to pass through the outermost pores of the nonwoven web material into the interior thereof while also ensuring that the agglomerated red blood cells will be unable to pass through the pores to contact superabsorbents which my be present.

The porsous nonwoven web material of this invention may be produced by any method known to those skilled in the art for producing nonwoven web materials. The fibers from which the nonwoven web material of this invention is made may be produced, for example, by meltblowing or spunbonding processes, including those processes producing bicomponent, biconstituent or polymer blend fibers which are well known in the art. These processes generally use an extruder to supply melted thermoplastic polymer to a spinneret where the polymer is fiberized to yield fibers which may be staple length or longer. The fibers are then drawn, usually pneumatically, and deposited on a moving foraminous map or belt to form the nonwoven fabric. The fibers produced in the spunbond and meltblown processes are microfibers.

Alternatively, the nonwoven web may be a bonded carded web. Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form generally machine direction-oriented fibrous nonwoven web. Once the web is formed, it is then bonded by one or more of several known bonding methods. One such bonding method is powder bonding wherein a powdered adhesive is distributed through the web and then activated, usually by heating the web and adhesive with hot air. Another suitable bonding method is pattern bonding wherein heated calendar rolls or ultrasonic bonding equipment are used to bond the fibers together, usually in localized bond pattern, though the web can be bonded across its entire surface, if so desired. Another suitable bonding method, particularly when using bicomponent staple fibers, is through-air bonding.

In accordance with one preferred embodiment of this invention, the nonwoven web material of this invention is a multilayer laminate in which nonwoven web material layers having different average pore sizes are layered on e upon another so as produce a nonwoven web material having a porosity gradient as defined hereinabove.

To provide separation of the red blood cells from the blood-containing fluids absorbed into the personal care absorbent article in accordance with one embodiment of this invention, the porous nonwoven web material is treated with a fluid treatment agent which is an agglomerating agent which causes the red blood cells to clump upon coming into contact with the agglomerating agent. Suitable agglomerating fluid treatment agents for use in the personal care absorbent article of this invention include, but are not limited to, antibodies, polycationic materials, that is highly positively charged polymers, and tri-block copolymers of polypropylene oxide and polyethylene oxide. One particularly suitable tri-block copolymer goes under the commercial name of PLURONIC® F-98 available from BASF (Germany) and constitutes a particularly preferred embodiment of the invention. PLURONIC F-98 is a tri-block copolymer surfactant of 80% by weight polyethylene oxide and 20% by weight polypropylene oxide having a molecular weight of about 9000.

Investigations which we have conducted have shown that greater than about a 1% by weight PLURONIC F-98 solution is required to agglomerate red blood cells in blood and menses. In accordance with a particularly preferred embodiment of this invention, the agglomerating fluid treatment agent is a 2% by weight solution of PLURONIC F-98.

EXAMPLE

One gram of a 20% solution of PLURONIC® F-98 was mixed with blood and 3 grams of the resulting mixture were applied to a piece of polyethylene film. After five minutes, the blood was drained off. Observation of the "treated" blood under a microscope revealed that the red blood cells had agglomerated without lysing.

As a result of treatment of the porous nonwoven web material with an agglomerating fluid treatment agent, the red blood cells clump together and are "filtered" out of the menses or blood ads a result of being trapped in the pores of the nonwoven web material. In accordance with on preferred embodiment of this invention, the nonwoven web material comprises a porosity gradient which acts as a "depth filter". The remaining fluid, without the red blood cells, is less colored, as a result of which any leakage which may occur is not as easily detected. In addition, the uptake of the menses by the nonwoven web material and the superabsorbents which may be present without the red blood cells is improved compared to menses in which the red blood cells are present because the red blood cells are no longer available for clogging passages in the nonwoven web material (wicking material) and superabsorbents. Finally, in the absence of red blood cells, the menses exhibits reduced viscoelastic properties, that is improved fluid intake, distribution and absorption properties.

Our finding that a surfactant such as the tri-block copolymer surfactant PLURONIC F-98 can be used as a red blood cell agglomerating agent without lysing of the red blood cells is particularly unusual and unexpected because surfactant as a whole are known to lyse red blood cells. To our knowledge, until now, surfactant which enable the agglomeration of red blood cells without lysing were not known.

In addition to PLURONIC copolymer surfactant, in accordance with one embodiment of this invention, the agglomerating fluid treatment agent comprises at least one antibody. Methods for obtaining antibodies suitable for use in this invention are generally known to those skilled n the art and typically involve injection of red blood cell membranes into an animal, resulting in generation of the antibody by the animal, and harvesting of the antibody from the animal.

In accordance with yet another embodiment of this invention, the fluid treatment agent is a polycationic polymer surfactant, that is, a highly positively charged linear polymer. One example of a polycationic polymer suitable for use as a fluid treatment agent in accordance with one preferred embodiment of this invention is polylysine.

In accordance with on preferred embodiment of this invention, the fluid treatment agent applied to the nonwoven web material is a red blood cell lysing agent. We have found that at least some lysing agents in accordance with this invention are effective in their ability to lyse red blood cells at concentrations as low as 0.1% by weight. Suitable lysing agents for use in the personal care absorbent articles of this invention include GLUCOPON 220, an octylpolyglycoside available from Henkel Corporation, Ambler, Pa., MASIL® SF-19, an alkoxylated polysiloxane available from PPG Industries, Inc., Specialty Chemicals Division, Gurnee, Ill., nonionic surfactant LAURETH 7, an alkoxylated alcohol available from Heterene, Inc., Paterson, N.J., nonionic LAURETH 4, an alkoxylated alcohol available from Heterence, Inc., nonionic PPG 5-Laureth 5, an alkoxylated alcohol available from Henkel Corporation, amphoteric surfactant DERIPHAT 160S, an alkyl-substituted amino acid available from Henkel/Cospha, Ambler, Pa., anionic surfactant sodium laurel sulfate, an alkyl sulfate available from Henkel, amphoteric MACKAM 15-L, an alkyl substituted amino acid available from McIntyre Group, University Park Ill., anionic MACKANATE LM-40, a sulfosuccinate available from McIntyre Group, anionic STANDOPOL SH124-3, a sulfosuccinate available from Henkel/Cospha, and anionic HAMPOSYL L-30, a sarcosinate available from Hampshire Chemical, Lexington, Mass.

In accordance with a particularly preferred embodiment of this invention, the red blood cell lysing agent is a saponin, a high molecular weight glycoside comprising a sugar part linked to a triterpene or steroid aglycone. A suitable saponin produced from quillaja bark is available from Sigma Chemical Company, St. Louis, Mo.

A method for producing an absorbent material for facilitating fluid handling and providing reduced staining in personal care absorbent articles comprises forming a nonwoven web material having an average pore size in the range of about 10 microns to about 200 microns and treating said nonwoven web material with a fluid treatment agent, which fluid treatment agent is preferably an agglomerating agent suitable for causing red blood cells in a blood-containing fluid to agglomerate upon contact with the agglomerating agent or a red blood cell lysing agent. Suitable agglomerating agents include PLURONIC® F-98, antibodies, and polycationic polymers. The fluid treatment agent may be applied to the nonwoven web material by any means known to those skilled in the art including dipping the nonwoven web material into a solution of the fluid treatment agent or spraying the fluid treatment agent directly onto the nonwoven web material.

While in the foregoing specification the invention has been description in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A personal care absorbent article comprising:
   a porous nonwoven web material treated with a soluble fluid treatment agent suitable for altering red blood cells on contact with a red blood cell-containing fluid, said porous nonwoven web material having an average pore size in a range of about 10 microns to about 200 microns, wherein said agent comprises a tri-block copolymer comprising polypropylene oxide and polyethylene oxide.

2. A personal care absorbent article in accordance with claim 1, wherein said agent further comprises a polycationic material.

3. A personal care absorbent article in accordance with claim 2, wherein said polycationic material comprises a polycationic surfactant linear polymer.

4. A personal care absorbent article in accordance with claim 2, wherein said polycationic material comprises polylysine.

5. A personal care absorbent article in accordance with claim 1, wherein said fluid treatment agent further comprises an antibody.

6. A personal care absorbent article in accordance with claim 1, wherein said fluid treatment agent further comprises a saponin.

7. A personal care absorbent article in accordance with claim 1, wherein said porous nonwoven web material comprises a porosity gradient with pore size increasing from one size porous nonwoven web material to an opposite side of said porous nonwoven web material.

8. A personal care absorbent article in accordance with claim 1, wherein said porous nonwoven web material is a nonwoven material selected from the group consisting of spunbond, meltblown, airlaid, and bonded carded.

9. A personal care absorbent article in accordance with claim 1, wherein said fluid treatment agent comprises a solution comprising greater than about 1% by weight of said tri-block copolymer.

10. A personal care article in accordance with claim 1 further comprising at least one superabsorbent dispersed throughout said nonwoven web material.

11. A personal care absorbent article in accordance with claim 1, wherein said fluid treatment agent further comprises an alkoxylated alcohol.

12. A personal care absorbent article in accordance with claim 1, wherein said fluid treatment agent further comprises an octylpolyglycoside.

13. An absorbent material comprising:
   a backing material which is substantially fluid impervious;
   a cover material comprising a fluid permeable polymeric film; and
   an absorbent core disposed between said cover material and said backing material, said absorbent core comprising a porous nonwoven web material treated with a soluble fluid treatment agent comprising a tri-block copolymer comprising polypropylene oxide and polyethylene oxide whereby red blood cells contacting said agent are one of agglomerated and lysed.

14. An absorbent material in accordance with claim 13, wherein said fluid treatment agent further comprises a polycationic material.

15. An absorbent material in accordance with claim 13, wherein said fluid treatment agent further comprises an antibody.

16. An absorbent material in accordance with claim 13, wherein at least one superabsorbent is disposed within said absorbent core.

17. An absorbent material in accordance with claim 13, wherein said porous nonwoven web material comprises a gradient of pore sizes with pore sizes decreasing in a direction of said backing material.

18. An absorbent material in accordance with claim 13, wherein said porous nonwoven web material comprises a nonwoven material selected from the group consisting of spunbond, meltblown, airlaid, and bonded carded.

19. An absorbent material in accordance with claim 13, wherein said fluid treatment agent comprises a solution comprising at least 1% by weight of said tri-block copolymer.

20. An absorbent material for absorption of a red blood cell containing viscoelastic fluid comprising:
   a porous synthetic substrate having a soluble fluid treatment agent comprising a tri-block copolymer comprising polypropylene oxide and polyethylene oxide disposed for contact by said viscoelastic fluid, whereby said red blood cells are one of agglomerated and lysed upon contact with said fluid treatment agent.

21. An absorbent material in accordance with claim 20, wherein said synthetic substrate comprises a nonwoven material.

22. An absorbent material in accordance with claim 21, wherein said nonwoven material is selected from the group consisting of spunbond, meltblown, airlaid and bonded carded.

23. An absorbent material in accordance with claim 20, wherein said fluid treatment agent comprises a polycationic compound.

24. An absorbent material in accordance with claim 20, wherein said fluid treatment agent comprises an antibody.

25. An absorbent material in accordance with claim 20, wherein said viscoelastic fluid comprises menses.

26. An absorbent material in accordance with claim 20, wherein said viscoelastic fluid comprises at least one of blood and wound exudate.

27. In a personal care absorbent article having a substantially fluid impervious backing material, a fluid permeable cover material, an absorbent core disposed between said cover material and said backing material, and a superabsorbent disposed within said absorbent core, the improvement comprising:
   said absorbent core comprising a porous nonwoven web material treated with a fluid treatment agent for altering red blood cells of a red blood cell-containing fluid upon contact with said absorbent core whereby said red blood cells are precluded from reducing a fluid uptake rate of said superabsorbent, said fluid treatment agent comprising a red blood cell agglomerating agent which comprises a surfactant selected from the group consisting of tri-block copolymers of polyethylene oxide and polypropylene oxide, and polycationic linear polymers.

28. A personal care absorbent article in accordance with claim 27, wherein said fluid treatment agent further comprises a red blood cell lysing agent disposed on said porous nonwoven web material.

29. A personal care absorbent article in accordance with claim 28, wherein said red blood cell lysing agent comprises a saponin.

30. A personal care absorbent article in accordance with claim 27, wherein said red blood cell agglomerating agent further comprises an antibody.

31. A personal care absorbent article in accordance with claim 27, wherein the pores of said porous nonwoven web material have an average pore size in a range of about 10 microns to about 200 microns.

32. A catamenial device comprising:
   a backing material which is substantially fluid impervious;
   a cover material comprising a fluid permeable polymeric film; and
   an absorbent core disposed between said cover material and said backing material, said absorbent core comprising a porous nonwoven web material treated with a soluble fluid treatment agent comprising a tri-block copolymer comprising polypropylene oxide and polyethylene oxide whereby red blood cells contacting said agent are one of agglomerated and lysed.

33. A material for absorption of a red blood-cell containing fluid comprising:
   an absorbent material treated with a soluble fluid treatment agent suitable for altering red blood cells on contact with said red blood cell-containing fluid, said soluble fluid treatment agent comprising a tri-block copolymer comprising polypropylene oxide and polyethylene oxide.

34. A material in accordance with claim 33, wherein said absorbent material comprises a nonwoven web material.

35. A material in accordance with claim 33, wherein said absorbent material comprises a woven material.

36. A material in accordance with claim 33, wherein said fluid treatment agent comprises at least one of a red blood cell agglomerating agent and a red blood cell lysing agent.

37. A material in accordance with claim 36, wherein said lysing agent comprises an alkoxylated alcohol.

38. A material in accordance with claim 36, wherein said lysing agent comprises an octylpolyglycoside.

39. A material in accordance with claim 33, wherein said agent further comprises a polycationic material.

40. A material in accordance with claim 39, wherein said polycationic material comprises a polycationic surfactant linear polymer.

41. A material in accordance with claim 39, wherein said polycationic material comprises polylysine.

42. A material in accordance with claim 33, wherein said fluid treatment agent further comprises an antibody.

43. A material in accordance with claim 33, wherein said fluid treatment agent further comprises a saponin.

44. A material in accordance with claim 33 further comprising at least one superabsorbent disposed within said absorbent material.

45. A wound dressing comprising:

an absorbent material treated with a soluble fluid treatment agent suitable for altering red blood cells on contact with said red blood cell-containing fluid, said soluble fluid treatment agent comprising a tri-block copolymer comprising polypropylene oxide and polyethylene oxide.

46. A wound dressing in accordance with claim 45, wherein said fluid treating agent comprises at least one of a red blood cell agglomerating agent and a red blood cell lysing agent.

* * * * *

UNITED STATES PATENT AND TRADEMARK OFFICE
CERTIFICATE OF CORRECTION

PATENT NO. : 6,812,169 B2
DATED : November 2, 2004
INVENTOR(S) : David Charles Potts et al.

It is certified that error appears in the above-identified patent and that said Letters Patent is hereby corrected as shown below:

Column 8,
Line 64, replace "size" with -- side of said --.

Signed and Sealed this

Fifth Day of April, 2005

JON W. DUDAS
*Director of the United States Patent and Trademark Office*